United States Patent [19]

Elgas et al.

[11] Patent Number: 4,519,393
[45] Date of Patent: May 28, 1985

[54] FITTING FOR CORRUGATED TUBE

[75] Inventors: Roger J. Elgas, Littleton; Timothy M. Gordon, Morrison, both of Colo.

[73] Assignee: Cobe Laboratories, Inc., Lakewood, Colo.

[21] Appl. No.: 371,979

[22] Filed: Apr. 26, 1982

[51] Int. Cl.³ .............................................. A61F 7/00
[52] U.S. Cl. .................................... 128/400; 285/158; 285/355; 285/DIG. 4
[58] Field of Search ................. 285/DIG. 4, 355, 158; 128/400; 604/113

[56] References Cited

U.S. PATENT DOCUMENTS

| 3,078,109 | 2/1963 | Jackson et al. | 285/158 X |
| 3,146,142 | 8/1964 | Maly | 285/355 X |
| 3,366,504 | 1/1968 | Hulterstrum | 285/355 X |
| 4,065,264 | 12/1977 | Lewin | |
| 4,237,091 | 12/1980 | Lobdell et al. | 403/349 X |
| 4,431,219 | 2/1984 | Brewer et al. | 285/355 X |

FOREIGN PATENT DOCUMENTS

| 2241741 | 3/1975 | France | 285/DIG. 4 |
| 626423 | 10/1961 | Italy | 285/355 |

OTHER PUBLICATIONS

*Flexonics Engineering Guide No. 350*, pp. 1, 2, and 14–16; 1978.

*Primary Examiner*—Thomas F. Callaghan

[57] ABSTRACT

A fitting for connecting a helically corrugated heat exchanging tube to a source of heated fluid, the fitting having a plastic tubular member with an end adapted for connection to the source and an end with external helical threads formed on it, the threads being sized to provide a close clearance with the interior surface of the corrugated tube.

2 Claims, 9 Drawing Figures

FITTING FOR CORRUGATED TUBE STRUCTURE

FIELD OF THE INVENTION

The invention relates to fittings for corrugated heat exchanging tubes.

BACKGROUND OF THE INVENTION

Heat exchanging tubes are typically connected to a source of heated fluid, and placed in a container to permit flow of the fluid to be heated past exterior surfaces of the tubes. The tubes are often corrugated to increase surface area of the tube and heat transfer between the fluids. Some commercially available tubes have corrugations that are helical.

SUMMARY OF THE INVENTION

It has been discovered that a heat exchanging tube can be easily attached to a tubular fitting adapted to be connected to a source of heated fluid by providing an end of the fitting with external threads sized to provide a close clearance with the interior surface of the helically corrugated tube. The fitting can be easily screwed into the end of the tube, and the close clearance ensures that the fitting threads securely engage the tube.

In preferred embodiments the fitting has an extension on the end with the threads of smaller diameter than the internal diameter of the corrugated tube to facilitate connection of the two; potting is placed on the exterior surfaces of the threads prior to screwing it into the tube to provide a fluid-tight seal between them; the tube end passes through a hole in a blood heater casing, and there is provided a seal cover means having a flange conforming to the outside surface of the casing surrounding the hole and an extending portion with a hole in it through which the plastic fitting passes, and potting is injected between the exterior surface of the heating exchanging tube and the interior surface of the seal cover means, all to provide a liquid-tight seal between the fitting, heat exchanging tube and blood heater casing.

PREFERRED EMBODIMENT

The structure, construction and operation of the presently preferred embodiment of the invention will now be described, after first briefly describing the drawings.

DRAWINGS

STRUCTURE

Figure 1:
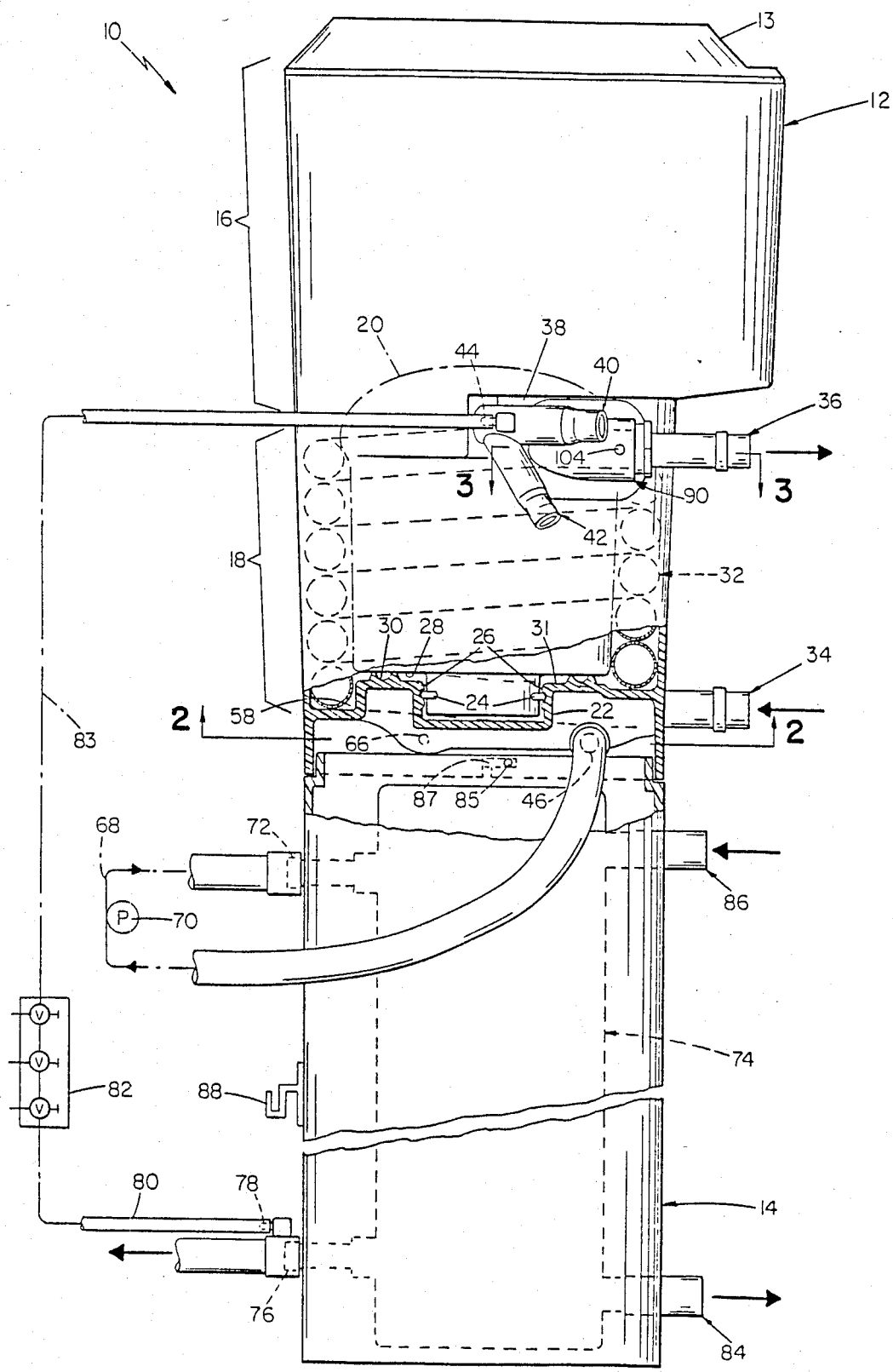
FIG. 1 is an elevation, somewhat diagrammatic and broken away, of blood oxygenating apparatus according to the invention.

Referring to FIG. 1 there is shown blood oxygenating apparatus 10 having upper molded polycarbonate casing 12, cap 13 and lower molded plastic support base 14. The portion of casing 12 designated 16 partially defines a blood reservoir storage region, and it is located on top of a portion 18 encasing the blood heating components. In the center of the blood heater is white molded-plastic central support member 20, which is connected to the bottom 22 of plastic casing 12 by threads 24 that interfere with protrusions 26 on casing 12. Polyurethane potting between the lower surface 28 of support member 20 and the upward facing annular groove 30 on lower horizontal portion 31 of casing 12 provides a seal between member 20 and casing 12.

Helically corrugated tube 32 is wound between central support 20 and housing 12. The tubing is made of stainless steel, is available from the Flexonics Division of UOP, Inc., Bartlett, Ill. as part no. 460L, is ultrasonically degreased before construction and has a pitch of approximately 0.134 inch, an exterior thread depth of about $\frac{1}{8}$ inch and an external diameter of approximately $\frac{3}{4}$ inch. The tubing makes $5\frac{1}{2}$ revolutions around member 20, and there is a small clearance between tubing 32, member 20 and casing 12. One end of tube 32 is sealably connected to plastic heated water inlet fitting 34, and the other end is similarly connected to identical heated water outlet fitting 36. Blood inlet 38 has port 40 for connection to a supply line of venous blood from the patient, port 42 for blood obtained from the patient's chest during surgery, and smaller return port 44 for connection to return line 83 of a sampling system, discussed in detail below. Blood inlet 38 enters casing 12 at a location just above the upper surface of the top winding of tube 32. At the bottom of heating portion 18 is blood outlet port 46, which is connected by tube 48 (FIG. 2) to the lowermost point of channel 58, which contains the lowermost winding of helically corrugated tube 32. Channel 58 is at its deepest near heated water inlet fitting 34; it gradually becomes more shallow as it extends clockwise (FIG. 2) around the circumference of the lower portion of plastic casing 12, and ends above the junction of tube 48 with its deepest portion. The shallow end of channel 58 is approximately even with the lower portion of center member 20.

Figure 2:
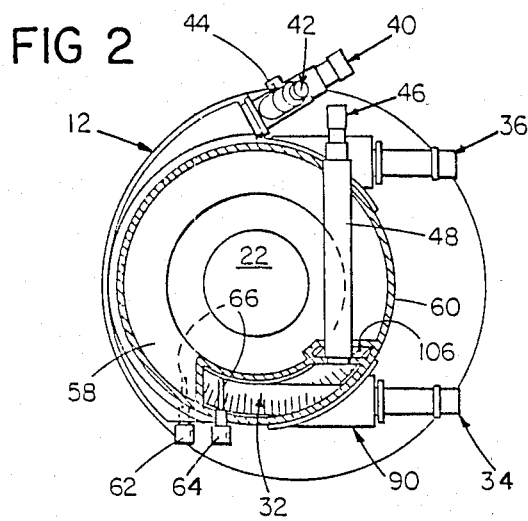
FIG. 2 is a horizontal sectional view, taken at 2—2 of FIG. 1, of the FIG. 1 apparatus.
Figure 5:
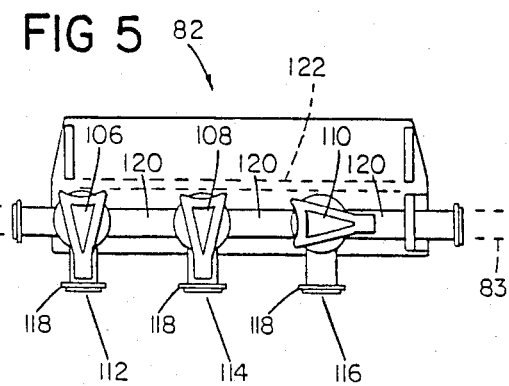
FIG. 5 is a plan view of a sampling access device of the FIG. 1 apparatus.

Referring to FIG. 2, sockets 62, 64 (of the type disclosed in U.S. Pat. No. 4,237,091) for temperature probes are provided in heating portion 18. Socket 64 is in a recess in channel 58 below tube 32 located just upstream of the junction of tube 48 and channel 58. Socket 62 is located about $\frac{1}{8}$ inch above the highest winding of heat exchanger tube 32. Both of these sockets are located on the opposite side of casing 12 from the side shown in FIG. 1. They have hollow plastic fittings extending out from the plastic casing 12, and hollow heat conducting portions 66 extending into the blood chamber within casing 12 at the top and bottom of heating portion 18. Thus, temperature probes (not shown) inserted into fittings 62, 64 will be isolated from the blood but in a heat conducting relationship with it.

Referring to FIG. 1, blood outlet 46 is connected by tube 68 to peristaltic pump 70 and blood inlet port 72 of membrane type fluid flow transfer device 74 (which is described in detail in a U.S. patent application entitled "Potting Seal For A Fluid Flow Transfer Device", filed simultaneously with this application by Roger J. Elgas and Gary A. Carson). Device 74 also has blood outlet port 76 for connection to a blood return line to the patient. Sample line port 78, for connection to sample tube 80 and sampling access device 82, described in detail below, is also connected to the blood return port 76. Within device 74 is a pleated semipermeable membrane (available from Celanese, Summit, N.J. under the trade designation Celgard 2402), a microporous sheet made of polypropylene with 0.2 by 0.02 micron holes. Microporous membranes suitable for use in transfer device 74 have pores sized large enough to allow air to pass through them at a higher rate than that of the slow molecular diffusion of homogeneous membranes, but small enough to prevent the flow of blood through them to the air channels at the transmembrane pressures achieved in the devices. The fold edges of the pleated sheet are potted to the housing of the device, and spacers are placed between adjacent folds. The pleated membrane defines alternate blood passages communicating with ports 72 and 76 and air passages communicating with air inlet port 86 and air outlet port 84. Device 74 is removably mounted within support base 14. On the side of base 14 is clip 88 to provide mounting for sampling device 82 when it is not detached from base 14.

Base 14 has a pair of protuberances 85 (one on each side), extending outwardly from the side wall near its top for mating with corresponding L-shaped slots 87 in casing 12 at its bottom.

Figure 3:
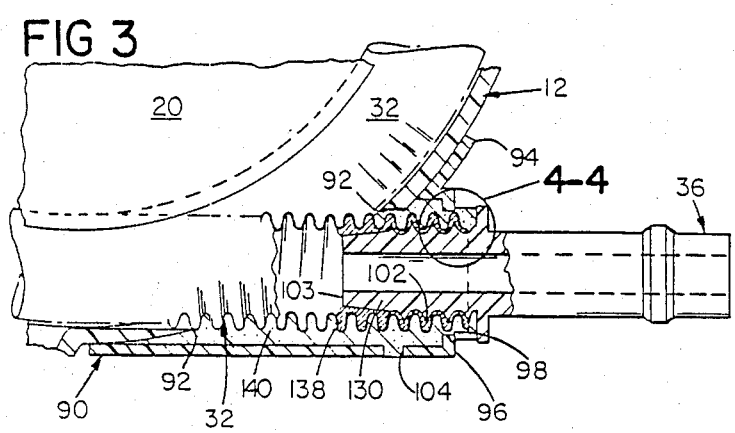
FIG. 3 is a horizontal sectional view, taken at 3—3 of FIG. 1, of a plastic fitting and its connection to said oxygenating apparatus.
Figure 6:
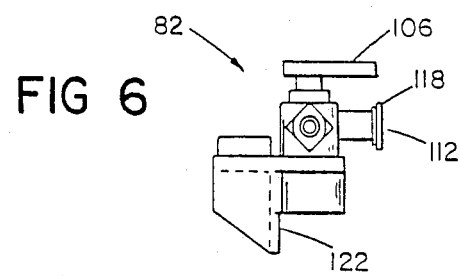
FIG. 6 is a side elevation of the FIG. 5 device.
Figure 4:
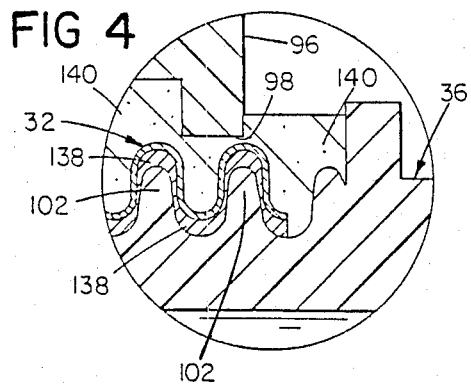
FIG. 4 is an enlarged, diagrammatic portion of the FIG. 3 view indicated at 4—4.

Referring to FIGS. 3 and 4, there is shown the sealable connections of fitting 36 and the end of tube 32 to each other and to housing 12. The end of tubing 32 extends through elliptical hole 92 in plastic casing 12. Tube cover seal 90 has a flange portion 94 completely surrounding hole 92 and extending portion 96 with circular hole 98 in its end. Plastic fitting 36 has external threads 102 formed on its interior end, generally conforming to the shape of, and providing a small clearance with, the interior surface of tube 32 to provide secure engagement between the tube and fitting. Fitting 36 also has nonthreaded extension 130 with a diameter smaller than the internal diameter of tube 32. Potting material 138 occupies the regions between the threads of fitting 36 and the interior surface of tube 32. Tube cover seal 90 is adhered to casing 12, and a liquid-tight seal is formed between the end of tube 32, casing 12, tube cover seal 90 and fitting 36 by polyurethane potting 140. Plastic fitting 34 is similarly connected to casing 12 near its bottom and to the other end of tube 32.

Figures 7, 8:
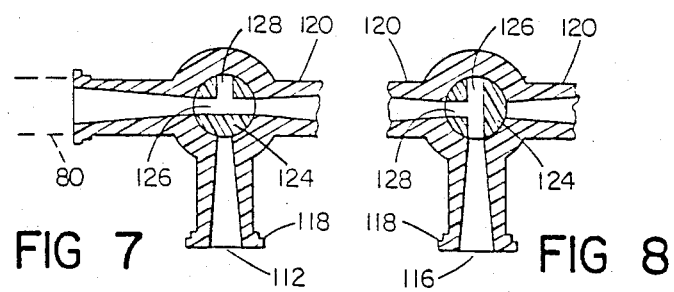
FIGS. 7 and 8 are schematic representations of sampling valves of the FIG. 5 sampling access device in different positions.

Referring to FIGS. 5 through 8, sampling access device 82 is shown connected to sample supply line 80 and return line 83 (in phantom). Three color-coded valve knobs 106, 108, 110 are shown with their associated sample ports 112, 114, 116, each having projections 118 for mating with teeth on sampling connectors (not shown). The three valves are connected in series between lines 80 and 83 by tubes 120. A vertical tab 122 mates with clip 88 when sampler 82 is mounted on the side of base 14. Valve knobs 106, 108 are in the nonsampling position, permitting flow of liquid from tube 80 through tubes 120. (FIG. 7 shows the corresponding orientation of rotatable flow director 124—connected to knob 106 or 108—with passage 126 directing flow between tubes 120, and transverse passage 128 being blocked.) Valve knob 110 is in one sampling position, diverting all flow from supply line 80 to sample port 116. (FIG. 8 shows the corresponding orientation of rotatable flow director 124 with passage 128 and 126 diverting flow to sample port 116 and blocking flow to downstream tube 120 and return line 83.) Another sampling position is with director in the position 180° from that in FIG. 7.

Figure 9:
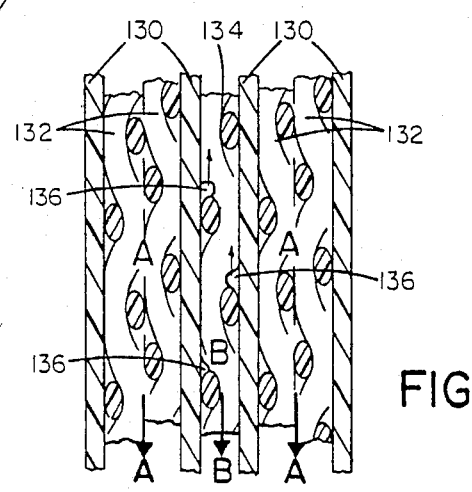
FIG. 9 is a diagrammatic vertical sectional view of an internal portion of a membrane device of the FIG. 1 apparatus.

Referring to FIG. 9, portions of adjacent air channels A and blood channel B are shown separated by pleated membrane 130. Spacers 132, 134 in channels A, B, respectively, space adjacent folds of membrane 130. Air bubbles 136 in blood channel B are shown adjacent to the center folds of membrane 130. The upward pointing arrow indicates the direction of the buoyancy force owing to the different densities of air and blood; the downward pointing arrow indicates the direction of travel of blood and air in the channels.

CONSTRUCTION

In constructing device 10 the blood heating components must be assembled within casing 12. First tube 32 is wound around central support member 20. Member 20 and tube 32 are then inserted into the heating portion 18 of housing 12, and member 20 is rotated so that threads 24 lock with projections 26, and the annular projections defining annular groove 30 contact surface 28. Potting is thereafter injected into groove 30 through holes (not shown) in horizontal portion 31 to seal member 20 to casing 12. The ends of tube 32 are pulled through holes 92 and sealed to fittings 34, 36 and casing 12. Adhesive is applied to the inner surface of flange 94 and corresponding areas of housing 12 around hole 92. Tube seal 90 is then placed against the outer wall of housing 12 with the end of tube 32 extending slightly from or being flush with hole 98. Potting is then applied to the exterior surfaces of threads 102, and fitting 36 is mated with tube 32. Smaller diameter extension 103 facilitates insertion and threading of fitting 36 with tube 32 and avoids blockage of the fitting's flow path by potting squeezed out from the threads. Additional potting is then injected through hole 104 (FIG. 1), which is covered by a tape during construction, into the regions between tube cover seal 90 and the exterior surface of tube 32 and wall 12. After the potting has cured, the tape is removed. Fitting 34 and its corresponding tube seal 90 is sealed to housing 12 in a similar manner. Temperature probe sockets 62, 64 are adhesively mounted in holes in casing 12. Tube 48 is inserted into a hole communicating with channel 58, and potting is poured into recess 106 (FIG. 2) to provide a seal. The valves in sampler 82 are constructed in a manner similar to that disclosed in U.S. Pat. No. 4,197,876, and the construction of membrane device 74 is described in the above-mentioned patent application.

OPERATION

To begin oxygenation, venous blood from a catheter or other source is supplied to the oxygenating apparatus through blood intake port 40 at a rate of approximately 5 to 6 liters per minute. The blood enters reservoir portion 16 and flows between the corrugations of heat exchanging tube 32 and casing 12 and member 20 in the heating portion 18. If the level of blood drops below the top of white central member 20, it becomes visible and provide a warning that the level is below a desired level. From heating portion 18 the blood is pumped by pump 70 into membrane device 74. (At the beginning, the blood may be recycled to the blood inlet to remove bubbles initially introduced into or formed within the apparatus.) A mixture of compressed air and oxygen is supplied to air port 86 of device 74 so that the pressure of the air within the membrane device is approximately 5 mm Hg above atmospheric pressure. The blood is pumped to result in a midline (there is a drop in pressure from the blood inlet to the blood outlet) blood pressure within device 74 of approximately 150 mm Hg above the pressure of air. Because the partial pressure of oxygen in the gas mixture is higher than that in the blood, oxygen will pass through the microporous membrane and become dissolved in the blood even though the blood pressure is higher than the air pressure. Because the blood flows downward through device 74, air bubbles that are accidentally introduced into it, e.g., bubbles 136 in FIG. 9, are generally detained near the top by buoyancy and are inhibited in their downward travel by spacer strands. Bubbles that do travel, do so at a slower velocity than that of the blood and have an increased residence time in the blood channel B. In any event, all air bubbles pass through the pores of the membrane to the gas side of the membrane, and introduction of gas bubbles into the patient's bloodstream is prevented. This removal of air bubbles from the blood results from maintaining the blood at a higher pressure than the air, using a microporous membrane, and employing the increased residence time provided by the spacer strands and the downflowing blood and upward directed buoyancy forces on the bubbles. The rate of passage of air bubbles through the membrane depends, in addition to these factors, on the blood surface tension, which depends upon the makeup of the blood, e.g., the concentration of red blood cells. Also, because the blood reservoir portion 16 is located above the membrane device 74, and the device is constructed as an integral unit, potential gas siphoning problems such as those that are caused when the blood reservoir is at a lower elevation than the membrane device during nonuse do not occur.

Oxygenated blood continuously flows through small diameter supply tube 80, sampler 82, and return line 83 at approximately 50 to 100 cc/min (compared with 5 to 6 liters per minute for the flow through the oxygenating apparatus 10) owing to the increased pressure at outlet port 76 caused by pump 70, and samples can be removed from access ports 112, 114, 116 on sampling device 82. Samples of oxygenated blood are supplied under pressure when any of the valves knobs are rotated to the position of knob 110, or when a knob is pointed away from its access port so that director 124 is 180° from its position in FIG. 7. If a sample of unoxygenated blood from blood inlet 38 is desired, the flow through line 80 must be blocked, and line 83 (approximately 15 cc in volume) flushed with unoxygenated blood prior to removing a sample. This can be done by connecting a syringe to port 114, turning its obstructor to a position 180° from that shown in FIG. 8 (thereby blocking flow from line 80), removing the oxygenated blood from line 83 with the syringe, turning the obstructor for valve 116 to the same position, and removing the unoxygenated sample from port 116. The blood pulled into the syringe to flush line 83 before sample removal can then be returned to the system. Because of the continuous flow through tube 80, clotting is avoided, and representative samples are guaranteed. Unsampled blood is not wasted but is returned via tube 83 to blood return port 44 and the blood reservoir in casing 12. Any air bubbles accidentally injected into the sampling system at sampling access device 82 are carried to the reservoir and removed from the blood. This is because flow to the outlet port 76, where the bubbles would be carried with the blood to a patient's bloodstream, is severely restrained by the continuous flow in tube 80 in the other direction, the distance from the sampler 82 to outlet port 76, and the increased pressure at port 76 relative to that at sampling device 82. Also, because tubes 80, 83 are flexible and long, sampling device 82 can be detached from clip 88 and moved to a convenient sampling location.

OTHER EMBODIMENTS

Other embodiments will be apparent to those in the art. For example, blood inlet port 38 could be connected near the top of casing 12 or to cap 13.

Also, a blood defoamer could be placed in the reservoir storage region in portion 16 to facilitate removal of bubbles introduced into the oxygenator.

OTHER INVENTIONS

Subject matter relating to the integral oxygenator construction was the joint invention of Gary A. Carson, Roger J. Elgas and Timothy M. Gordon, whose U.S. patent application entitled "Integral Blood Oxygenator" is being filed simultaneously with the present application.

Subject matter relating to the oxygenator sampling system was the joint invention of Gary A. Carson and Roger J. Elgas, whose U.S. patent application entitled "Sampling Device for Blood Oxygenator" is being filed simultaneously with the present application.

Subject matter relating to the oxygenator with downward blood flow past a microporous membrane was the joint invention of the inventors herein, and it is claimed in our U.S patent application entitled "Blood Oxygenator", which is being filed simultaneously with the present application.

We claim:

1. A blood heater comprising
   a casing having blood inlet means and blood outlet means and a hole through it, said casing providing a blood flow path from said inlet means to said outlet means,
   a helically corrugated tube made of heat conductive material within said casing, and having an end passing through said hole,
   a tubular member having an end adapted for connection to a source of heated fluid and an end with external helical threads formed on it connected to an end of said tube,
   said threads being sized to provide a small clearance with the interior surface of said corrugated tube,
   first potting material filling the voids between said threads and said interior surface,
   a seal cover means having a flange conforming to the outside surface of said casing surrounding said hole and an extending portion that ends near said end of said tube and has a hole through which said helically corrugated tube and tubular member pass, and
   second potting material sealing said outside surface surrounding said hole, said exterior surface of said tube, and the interior surface of said cover means to each other,
   said end of said helically corrugated tube being positioned outside of said blood flow path to direct any heated liquid leaking between said corrugated tube and tubular member outside of said casing.

2. The heater of claim 1 wherein said tubular member has an extension on the end with said threads, said extension having a diameter smaller than the internal diameter of said corrugated tube, and providing a space for excess said first potting material to prevent said first potting material from blocking the flow path of said corrugated tube.

* * * * *